United States Patent [19]

DiPietro et al.

[11] Patent Number: 5,649,901
[45] Date of Patent: Jul. 22, 1997

[54] KNEE BRACE

[76] Inventors: Mary DiPietro; Charles DiPietro, both of 15 Doherty Ave., Elmont, N.Y. 11003

[21] Appl. No.: 631,149

[22] Filed: Apr. 15, 1996

[51] Int. Cl.$^6$ .................................................. A61F 5/01
[52] U.S. Cl. .................................................. 602/26; 602/16
[58] Field of Search ........................... 602/5, 16, 23, 602/26, 62, 63

[56] References Cited

U.S. PATENT DOCUMENTS

| | | | |
|---|---|---|---|
| 1,851,241 | 3/1932 | Dresser | 602/16 X |
| 3,786,804 | 1/1974 | Lewis | 602/16 |
| 3,804,084 | 4/1974 | Lehman | 602/62 X |
| 3,923,047 | 12/1975 | Chant | 602/23 X |
| 3,935,858 | 2/1976 | Harroff | 602/62 X |
| 4,379,463 | 4/1983 | Meier et al. | 602/26 X |
| 4,887,590 | 12/1989 | Logue et al. | 602/26 |
| 4,941,462 | 7/1990 | Lindberg | 602/26 X |
| 5,085,210 | 2/1992 | Smith, III | 602/26 |
| 5,462,517 | 10/1995 | Mann | 602/5 X |
| 5,513,658 | 5/1996 | Goseki | 602/23 X |

*Primary Examiner*—Stephen R. Crow
*Assistant Examiner*—David R. Risley
*Attorney, Agent, or Firm*—Michael I. Kroll

[57] ABSTRACT

A knee brace (10) comprising a heavy duty surgical elastic bandage (12). A facility (14) is for binding the heavy duty surgical elastic bandage (12) in a removable manner about a knee of a leg (16) of a person (18). A structure (20) is built into the heavy duty surgical elastic bandage (12), for keeping in a first instance the leg (16) straight at the knee when standing, walking and sitting in a chair (22) and for allowing in a second instance the leg (16) to bend at the knee, to permit the person (18) to sit more comfortably in the chair (22).

2 Claims, 5 Drawing Sheets

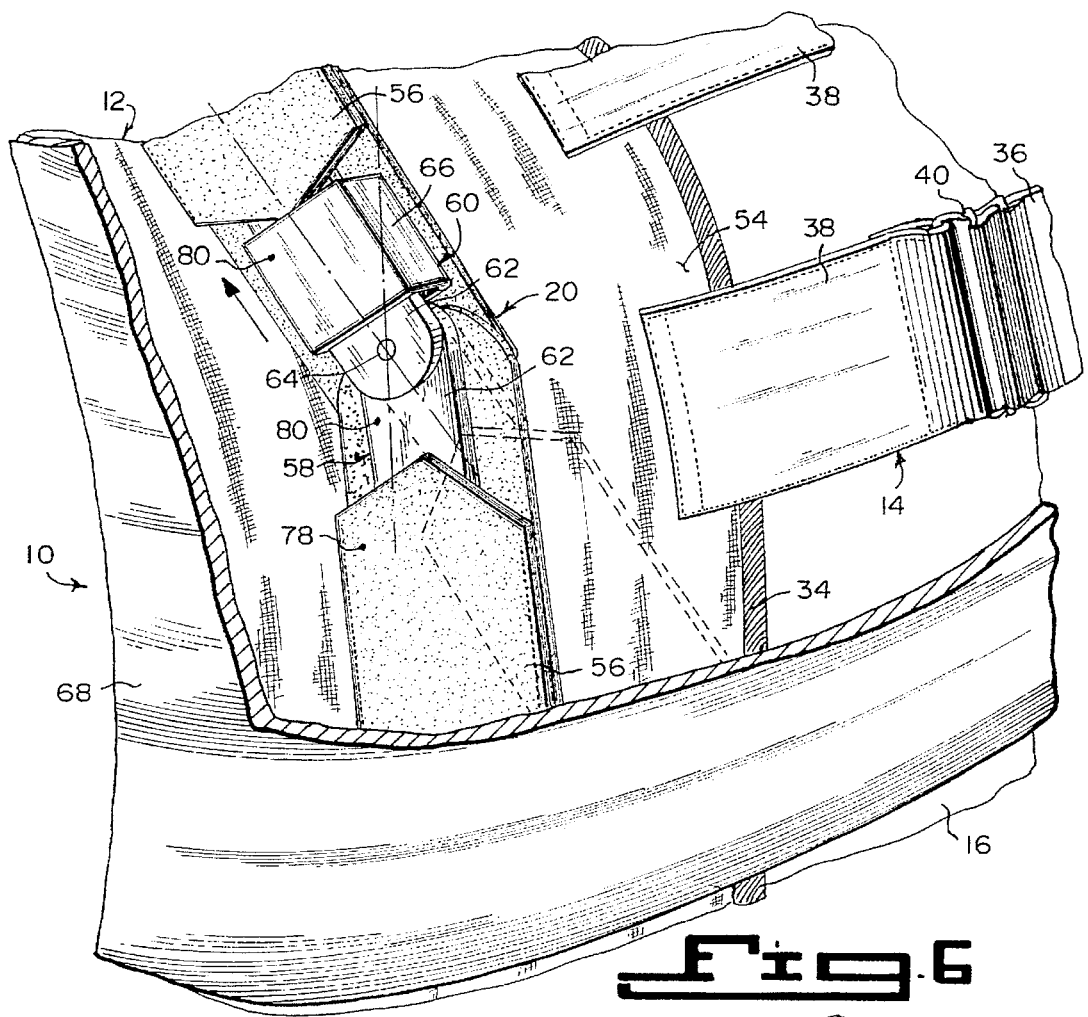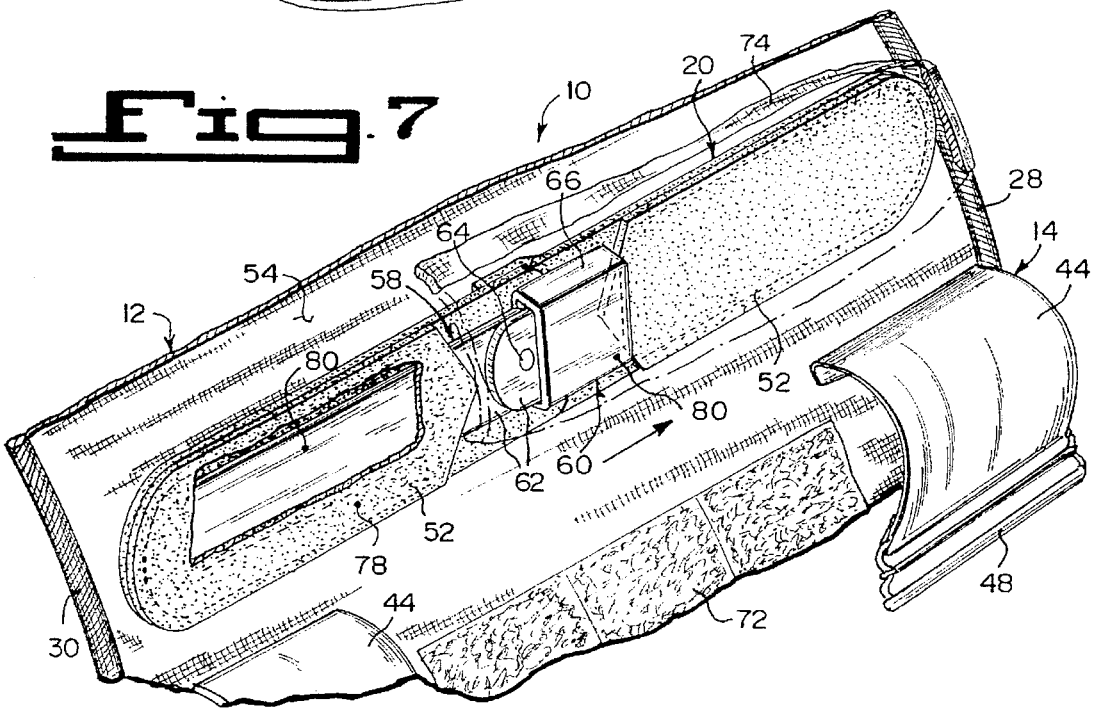

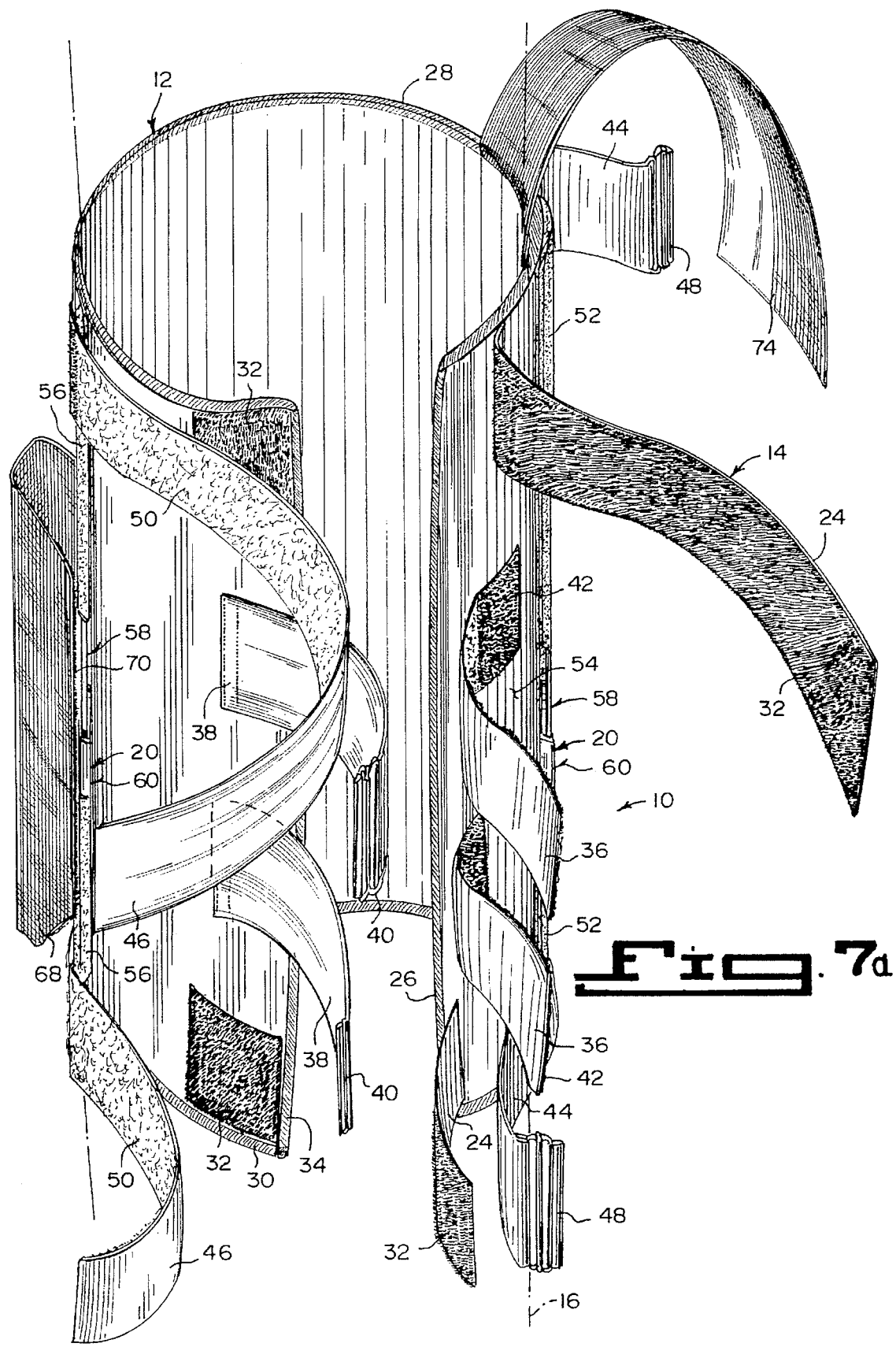

KNEE BRACE

BACKGROUND OF THE INVENTION

1. Field of the Invention

The instant invention relates generally to medical treatment aids and more specifically it relates to an a knee brace.

2. Description of the Prior Art

Numerous medical treatment aids have been provided in prior art. For example, bandages are generally strips of fabric used to bind up wounds or to keep dressings or compresses in place. Splints are any rigid materials used in conjunction with adhesive tapes to hold bones or limbs in fixed positions. While these units may be suitable for the particular purpose to which they address, they would not be as suitable for the purposes of the present invention as heretofore described.

SUMMARY OF THE INVENTION

A primary object of the present invention is to provide a knee brace that will overcome the shortcomings of the prior art devices.

Another object is to provide a knee brace that can be worn on a leg of a person and includes a pair of built-in hinged brackets, which when manually locked in place will support the knee area and keep the leg straight when standing, walking or sitting in a chair.

An additional object is to provide a knee brace, whereby when the pair of hinged brackets are manually unlocked, the leg will be allowed to bend at the knee, so as to permit the person to sit more comfortably in the chair.

A further object is to provide an a knee brace that is simple and easy to use.

A still further object is to provide a knee brace that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 6 is an enlarged perspective view of a portion of the instant invention with parts broken away, showing one of the hinged brackets unlocked to allow the leg to bend at the knee.

FIG. 7 is an enlarged perspective view of a portion of the instant invention with parts broken away, showing one of the hinged brackets locked to keep the leg straight at the knee.

FIG. 7a is a perspective view showing the instant invention ready to be installed about the knee of the leg, in which the leg is shown in phantom.

Similar reference characters denote corresponding features consistently throughout the attached drawings.

DETAILED DESCRIPTION OF THE PREFERRED EMBODIMENTS

Figure 1:
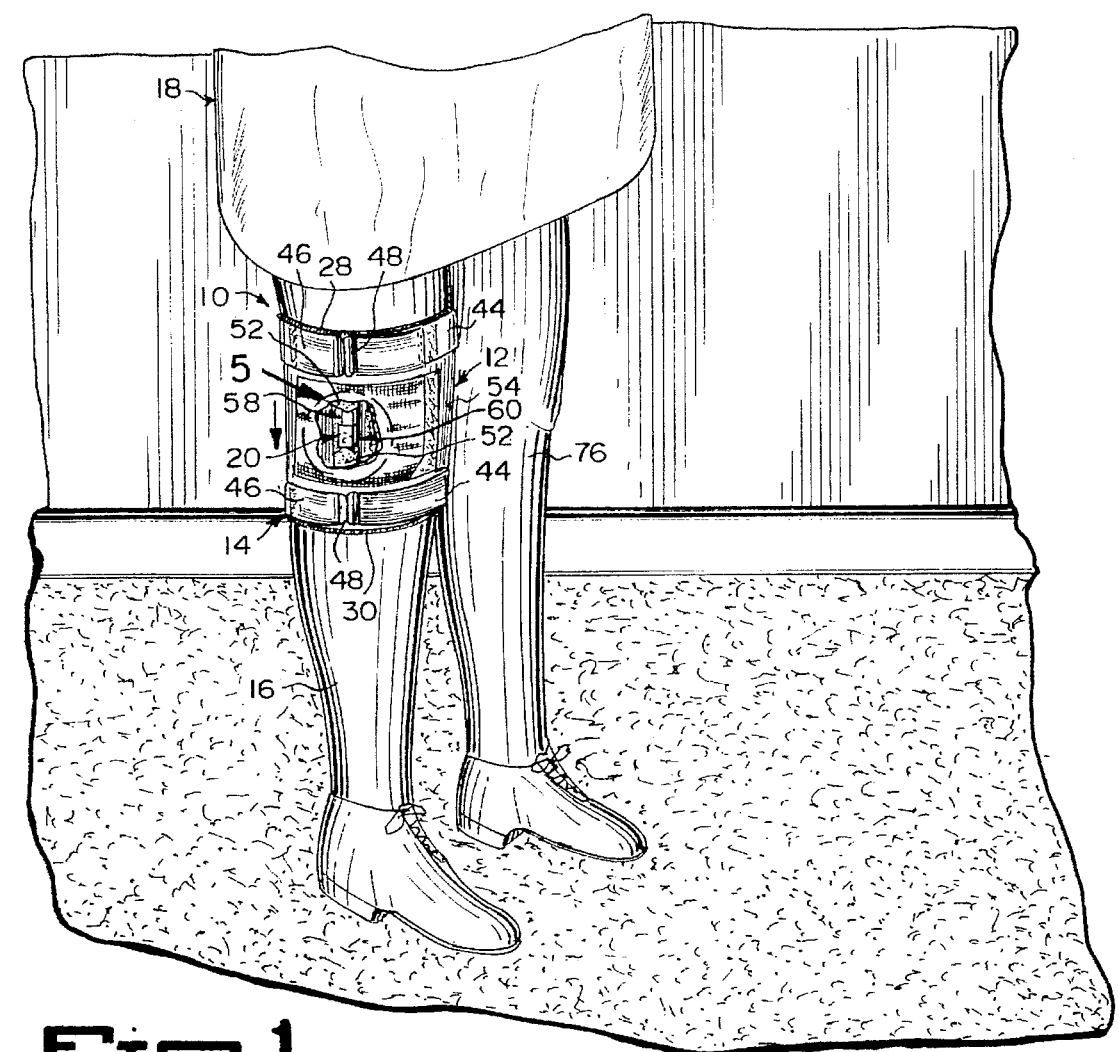
FIG. 1 is a perspective view of the instant invention worn about a knee of a leg of a person standing straight with parts broken away and hinged brackets locked to function as splints.
Figure 2:
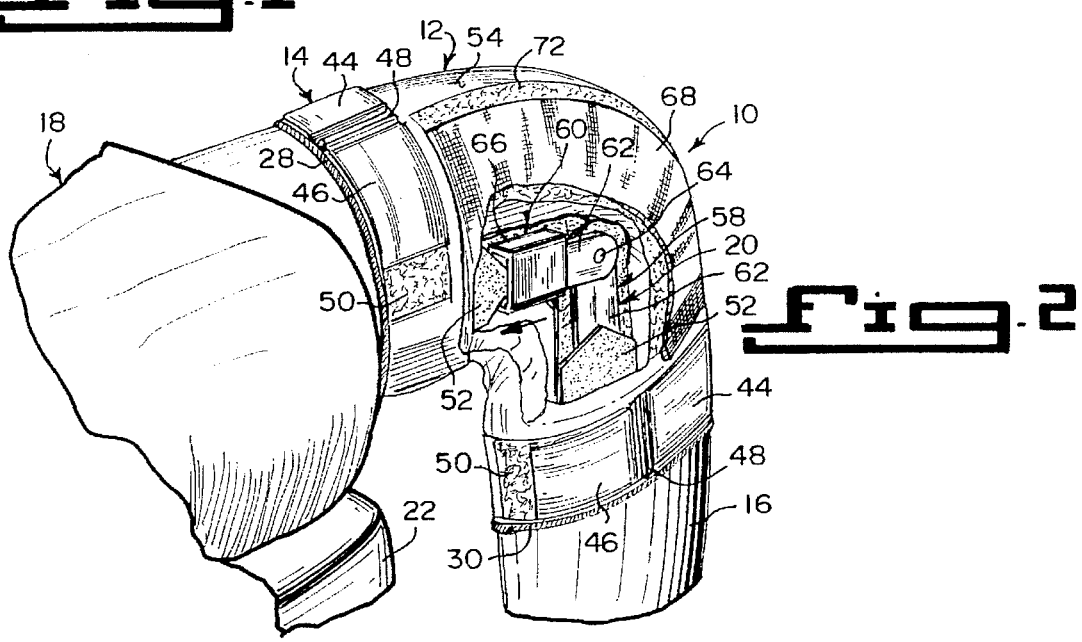
FIG. 2 is a perspective view of the instant invention worn about the knee of the leg of the person sitting in a chair with parts broken away, the hinged brackets unlocked and the leg bent at the knee.
Figure 2A:
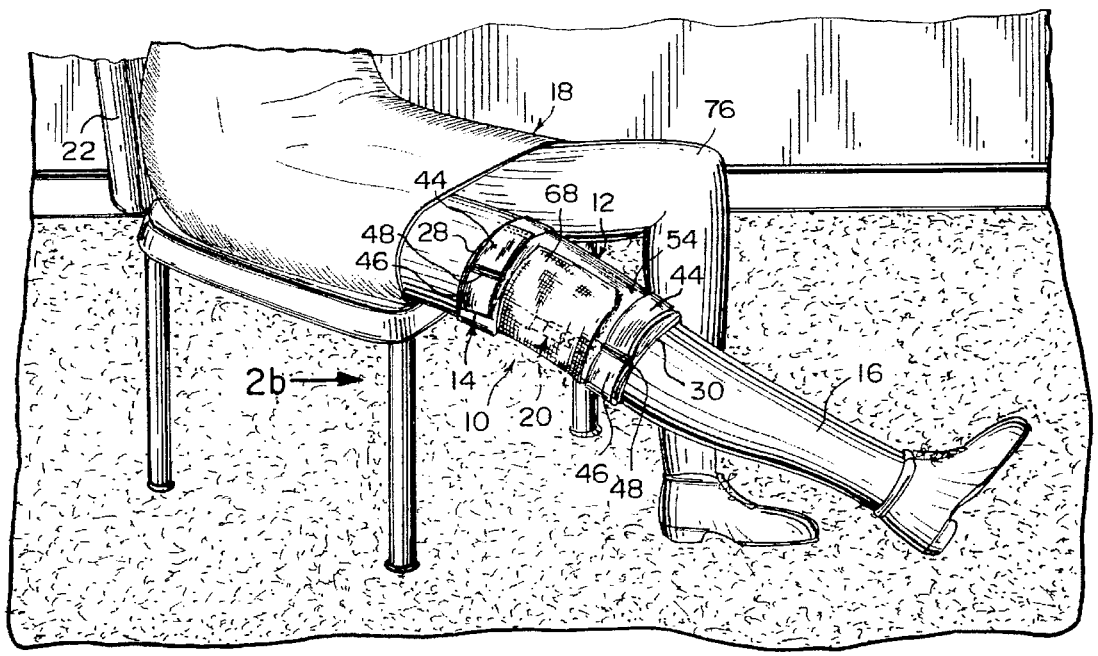
FIG. 2a is a perspective view of the instant invention worn about the knee of the leg of the person sitting in the chair, the hinged brackets locked and the leg straight at the knee.
Figure 2B:
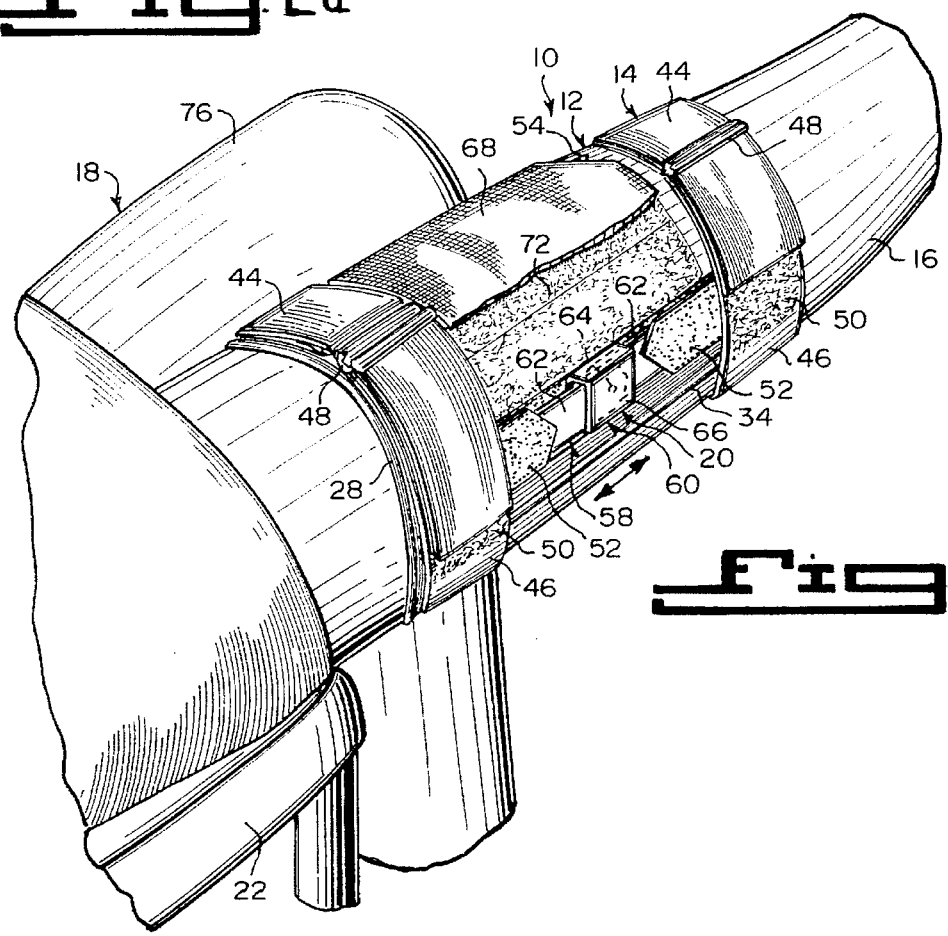
FIG. 2b is an enlarged perspective view taken in the direction of arrow 2b in FIG. 2a with parts broken away.
Figure 3:
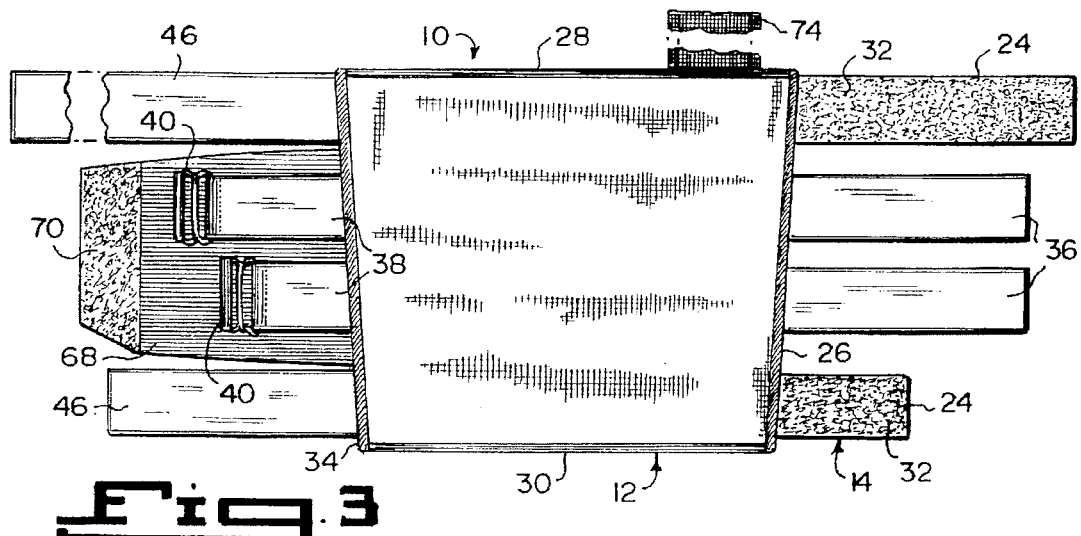
FIG. 3 is a reverse or inner plan view of the instant invention with parts broken away.
Figure 4:
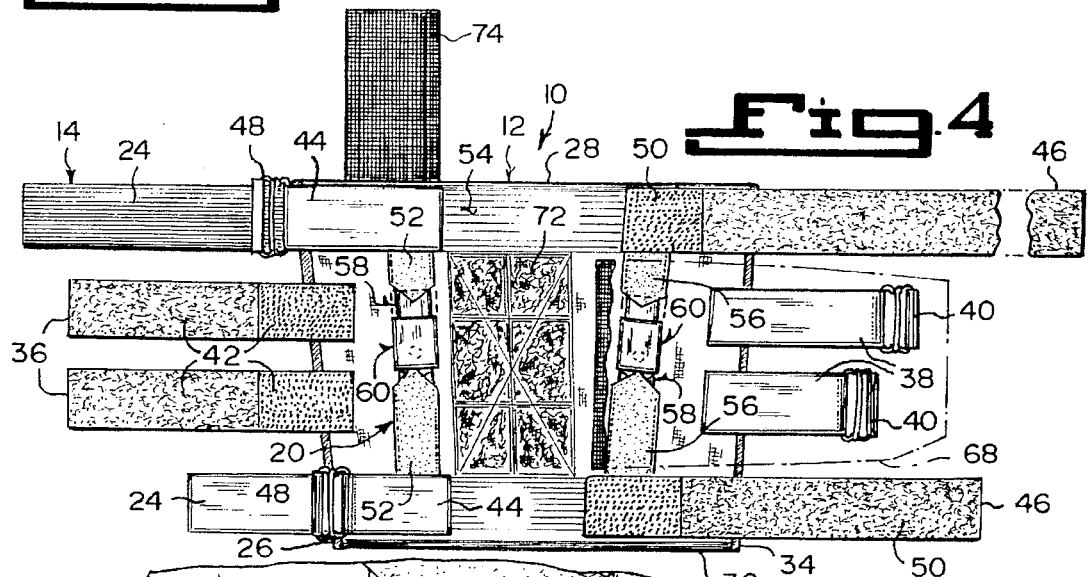
FIG. 4 is a front plan view of the instant invention with parts broken away.
Figure 5:
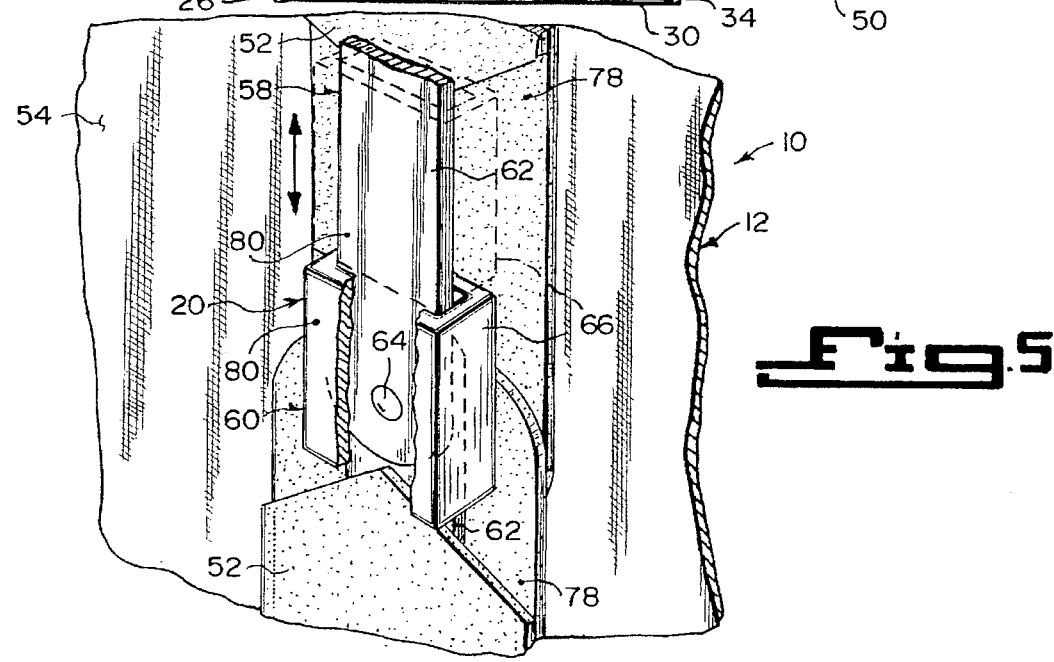
FIG. 5 is an enlarged perspective view of the area indicated by arrow 5 in FIG. 1.

Turning now descriptively to the drawings, in which similar reference characters denote similar elements throughout the several views, FIGS. 1 through 7a illustrate a knee brace 10 comprising a heavy duty surgical elastic bandage 12. A facility 14 is for binding the heavy duty surgical elastic bandage 12 in a removable manner about a knee of a leg 16 of a person 18. A structure 20 is built into the heavy duty surgical elastic bandage 12, for keeping in a first instance the leg 16 straight at the knee when standing, walking and sitting in a chair 22 and for allowing in a second instance the leg 16 to bend at the knee, to permit the person 18 to sit more comfortably in the chair 22.

The binding facility 14 includes two bands 24 extending from a first side edge 26 of the heavy duty surgical elastic bandage 12. One band 24 is near a top edge 28 and the other band 24 near a bottom edge 30 of the heavy duty surgical elastic bandage 12. Hook and loop type fasteners, such as, for example, VELCRO® 32 removably attach loose ends of the bands 26 to a second side edge 34 of the heavy duty surgical elastic bandage 12, when the heavy duty surgical elastic bandage 12 is wrapped about the knee of the leg 16 of the person 18.

Two straps 36 extend from the first side edge 26 of the heavy duty surgical elastic bandage 12 between the two bands 24. Two straps 38 extend from the second side edge 34 of the heavy duty surgical elastic bandage 12, which are in alignment with the two straps 36 on the first side edge 26. A pair of buckles 40 are each secured to a distal free end of each of the two straps 38 on the second side 34. Loose ends of the two straps 36 on the first side edge 26 can be retained in an adjusted manner in the buckles 40, after the heavy duty surgical elastic bandage 12 is wrapped about the knee of the leg 16 of the person 18. Hoop and loop type fasteners 42 are on the two straps 36 on the first side edge 26, to hold the loose ends together when inserted through the buckles 40 and looped back thereupon.

Two belts 44 extend from the first side edge 26 of the heavy duty surgical elastic bandage 12 over the two bands 24. Two belts 46 extend from the second side edge 34 of the heavy duty surgical elastic bandage 12, which are in alignment with the two belts 44 on the first side edge 26. A pair of buckles 48 are each secured to a distal free end of each of the two belts 44 on the first side edge 26. Loose ends of the two belts 46 on the second side edge 34 can be retained in an adjusted manner in the buckles 48. Hook and loop type fasteners 50 are on the two belts 46 on the second side edge 34, to hold the loose ends together when inserted through the buckles and looped back thereupon.

The structure 20 for keeping the leg straight and for allowing the leg to bend at the knee consists of a first pair of sheaths 52 secured to an outer surface 54 at the first side edge 26 of the heavy duty surgical elastic bandage 12. The first pair of sheaths 52 are parallel to the first side edge 26 and face each other. A second pair of sheaths 56 are secured to the outer surface 54 at the second side edge 34 of the heavy duty surgical elastic bandage 12. The second pair of sheaths 56 are parallel to the second side edge 34 and face each other. A pair of hinged brackets 58 are provided. The first hinged bracket 58 fits into the first pair of sheaths 52. The second hinged bracket 58 fits into the second pair of sheaths 56.

A pair of slide locks 60 are also provided. The first slide lock 60 fits onto the first hinged bracket 58. The second slide lock 60 fits onto the second hinged bracket 58. The slide locks 60 can be manually moved in a first direction, to prevent the hinged brackets 58 from pivoting. The slide locks 60 can be manually moved in a second direction, to allow the hinged brackets 58 to pivot.

Each hinged bracket 58 includes a pair of flat arms 62. Each flat arm 62 fits into one sheath 52 or 56. A rivet 64 pivotally connects overlapping ends of the flat arms 62 together. Each slide lock 60 is a rectangular shaped sleeve 66, which will slide over the rivet 64 at the overlapping ends of the flat arms 62 in the first direction and slide away from the rivet 64 at the overlapping ends of the flat arms 62 in the second direction.

A surgical elastic band cover 68 is attached along a first side to the outer surface 54 of the heavy duty surgical elastic bandage 12, so as to extend over the second pair of sheaths 56, the second hinged bracket 58 and the second slide lock 60. A first hook and loop type fastener 70 is affixed to a second side of the surgical elastic band cover 68. A second hook and loop type fastener 72 is secured centrally to the outer surface 54 of the heavy duty surgical elastic bandage 12. When the surgical elastic band cover 68 is wrapped thereabout, the first hook and loop type fastener 70 will mate with the second hook and loop type fastener 72.

An elastic flap member 74 can be affixed to the top edge 28 of the heavy duty surgical elastic bandage 12. The elastic flap member 74 can be folded down to cover over the first pair of sheaths 52, the first hinged bracket 58 and the first slide lock 60, to reduce rubbing against other the leg 76 of the person 18. The sheaths 52 and 56 are each fabricated out of leather material 78, while the hinged brackets 58 and the slide locks 60 are each fabricated out of metal material 80.

LIST OF REFERENCE NUMBERS 10 knee brace
12 heavy duty surgical elastic bandage of 10
14 binding facility of 10
16 leg of 18
18 person
20 structure for keeping the leg straight and for allowing the leg to bend at the knee of 10
22 chair
24 band of 14 at 26
26 first side edge of 12
28 top edge of 12
30 bottom edge of 12
32 VELCRO fastener of 14 for 24
34 second side edge of 12
36 strap of 14 at 26
38 strap of 14 at 34
40 buckle of 14 on 38
42 hook and loop type fastener on 36
44 belt of 14 at 26
46 belt of 14 at 34
48 buckle of 14 on 44
50 hook and loop type fastener of 14 for 46
52 sheath of 20
54 outer surface of 12
56 sheath of 20
58 hinged bracket of 20
60 slide lock of 20
62 flat arm of 58
64 rivet of 58
66 rectangular shaped sleeve for 60
68 surgical elastic band cover
70 first hook and loop type fastener on 68
72 second hoop and loop type fastener on 54 of 12
74 elastic flap member on 28
76 other leg of 18
78 leather material for 52 and 56
80 metal material for 58 and 60

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A knee brace comprising;
   a) a heavy duty surgical elastic bandage;
   b) means for binding said heavy duty surgical elastic bandage in a removable manner about a knee of a leg of a person, said binding means including;
      i) two bands extending from a first side of said heavy duty surgical elastic bandage with an upper band near a top edge and a lower band near a bottom edge of said heavy duty surgical elastic bandage, with hook and loop type fasteners on loose ends of said bands and a second side of said heavy duty surgical elastic bandage to removably attach said loose ends to said second side of said heavy duty surgical elastic bandage, when said heavy duty surgical elastic bandage is wrapped about the knee of the leg of the person;
      ii) two straps extending from the first side edge of said heavy duty surgical elastic bandage between said two bands;
      iii) two straps extending from the second side edge of said heavy duty surgical elastic bandage, which are in alignment with said two straps on the first side edge;

iv) a pair of buckles each secured to distal free ends of each of said two straps on the second side edge, so that loose ends of said two straps on the first side can be retained in an adjustable manner in said buckles, after said heavy duty surgical elastic bandage is wrapped about the knee of the leg of the person; and v) hook and loop type fasteners on said two straps on the first side edge, to hold the loose ends together when inserted through said buckles and looped back thereupon;

vi) two belts extending from the first side edge of said heavy duty surgical elastic bandage over said two bands;

vii) two belts extending from the second side edge of said heavy duty, surgical elastic bandage which are in alignment with said two belts on the first side edge;

viii) a pair of buckles each secured to a distal free end of each said two belts on the first side edge, so that loose ends of said two belts on the second side edge can be retained in an adjustable manner in said buckles; and ix) hook and loop type fasteners on said two belts on the second side edge to hold the loose ends together when inserted through said buckles and looped back thereupon;

c) means built into said heavy duty surgical elastic bandage for keeping in a first instance, the leg straight at the knee when standing walking and sitting, and for allowing, in a second instance, the leg to bend at the knee, to permit the person to sit more comfortably, said means including:

i) a first pair of sheaths secured to an outer surface at a first side edge of said heavy duty surgical elastic bandage, so that said first pair of sheaths are parallel to the first side edge and face each other;

ii) a second pair of sheaths secured to the outer surface at a second side edge of said heavy duty surgical elastic bandage, so that said second pair of sheaths are parallel to the second side edge and face each other;

iii) a pair of hinged brackets, whereby said first hinged bracket fits into said first pair of sheaths and said second hinged bracket fits into said second pair of sheaths, each said hinged bracket including: a pair of flat arms, in which each said flat arm fits into one said sheath; and a rivet to pivotally connect overlapping ends of said flat arms together; and iv) a pair of slide locks, whereby a first slide lock fits onto said first hinged bracket and a second slide lock fits onto said second hinged bracket, so that said slide locks can be manually moved in a first direction to prevent said hinged brackets from pivoting, while said slide locks can be manually moved in a second direction to allow said hinged brackets to pivot, each said slide lock being a rectangular shaped sleeve slideable over said rivet at the overlapping ends of said flat arms in the first direction and slideable away from said rivet at the overlapping ends of said flat arms in the second direction;

d) a surgical elastic band cover attached along a first side to the outer surface of said heavy duty surgical elastic bandage, so as to extend over said second pair of sheaths, said second hinged bracket and said second slide lock;

e) a first hook and loop type fastener affixed to a second said surgical elastic band cover;

f) a second hook and loop type fastener secured centrally to the outer surface of said heavy duty surgical elastic bandage, so that when said surgical elastic band cover is wrapped thereabout, said first hook and loop type fastener will mate with said second hook and loop type fastener; and g) an elastic flap member affixed to a top edge of said heavy duty surgical elastic bandage, whereby said elastic flap member can be folded down to cover over said first pair of sheaths, said first hinged bracket and said first slide lock, to reduce rubbing against an other leg of the person.

2. A knee brace as recited in claim 1, wherein said sheaths are each fabricated out of leather material, while said hinged brackets and said slide locks are each fabricated out of metal material.

* * * * *